United States Patent
Takigahira et al.

(10) Patent No.: US 12,053,157 B2
(45) Date of Patent: Aug. 6, 2024

(54) ENDOSCOPE

(71) Applicants: Fujikura Ltd., Tokyo (JP); FiberTech Co., Ltd., Chiba (JP)

(72) Inventors: Masato Takigahira, Sakura (JP); Yusuke Matsuda, Sakura (JP)

(73) Assignees: Fujikura Ltd., Tokyo (JP); FiberTech Co., Ltd., Chiba (JP)

( * ) Notice: Subject to any disclaimer, the term of this patent is extended or adjusted under 35 U.S.C. 154(b) by 85 days.

(21) Appl. No.: 17/211,238

(22) Filed: Mar. 24, 2021

(65) Prior Publication Data
US 2021/0298580 A1   Sep. 30, 2021

(30) Foreign Application Priority Data
Mar. 26, 2020   (JP) .................. 2020-056092

(51) Int. Cl.
*A61B 1/00*   (2006.01)

(52) U.S. Cl.
CPC ...... *A61B 1/00137* (2013.01); *A61B 1/00006* (2013.01); *A61B 1/00057* (2013.01); *A61B 1/00101* (2013.01); *A61B 1/00144* (2013.01)

(58) Field of Classification Search
CPC ............ A61B 1/00089; A61B 1/00101; A61B 1/00103; A61B 1/00135; A61B 1/00142; A61B 1/00144; A61B 1/0008
See application file for complete search history.

(56) References Cited

U.S. PATENT DOCUMENTS

| | | | | |
|---|---|---|---|---|
| 4,831,437 A | * | 5/1989 | Nishioka | A61B 1/042 348/649 |
| 5,570,129 A | * | 10/1996 | Hafele | H04N 9/73 348/E9.051 |
| 5,725,475 A | * | 3/1998 | Yasui | A61B 1/127 600/129 |
| 7,717,630 B1 | * | 5/2010 | Wan | G03B 17/00 396/448 |
| 9,667,935 B2 | * | 5/2017 | Salman | A61B 1/00181 |
| 11,298,001 B2 | * | 4/2022 | Mach | A61B 1/00096 |
| 2002/0010384 A1 | * | 1/2002 | Shahidi | A61B 5/06 600/117 |
| 2004/0249247 A1 | * | 12/2004 | Iddan | A61B 1/00183 600/170 |

(Continued)

FOREIGN PATENT DOCUMENTS

| | | |
|---|---|---|
| JP | S63-102746 A | 5/1988 |
| JP | 2002-051968 A | 2/2002 |

(Continued)

*Primary Examiner* — Matthew J Kasztejna
(74) *Attorney, Agent, or Firm* — Osha Bergman Watanabe & Burton LLP

(57) ABSTRACT

An endoscope includes: an endoscope operation unit; an insertion observation unit that extends forward from the endoscope operation unit in a longitudinal direction; and a protective cap that covers the insertion observation unit and is detachably attached to the endoscope operation unit. The protective cap includes a color index portion that adjusts white balance. The color index portion is disposed inside the protective cap at a position facing a tip of the insertion observation unit, and the color index portion includes a curved surface in a sectional view in the longitudinal direction of the insertion observation unit.

7 Claims, 7 Drawing Sheets

(56) References Cited

U.S. PATENT DOCUMENTS

| | | | |
|---|---|---|---|
| 2007/0142707 A1* | 6/2007 | Wiklof | A61B 1/00057 600/117 |
| 2007/0211274 A1* | 9/2007 | Donomae | H04N 1/60 358/1.9 |
| 2008/0228035 A1* | 9/2008 | Hagihara | A61B 1/127 600/176 |
| 2009/0221872 A1* | 9/2009 | Liddle | A61B 46/10 600/121 |
| 2011/0149057 A1* | 6/2011 | Beck | A61B 1/00057 348/E7.085 |
| 2014/0267656 A1* | 9/2014 | Blanquart | A61B 1/00137 348/68 |
| 2016/0015247 A1* | 1/2016 | Irion | A61B 1/00059 600/109 |
| 2018/0007346 A1* | 1/2018 | Ushijima | A61B 1/005 |
| 2019/0298154 A1 | 10/2019 | Mach et al. | |
| 2021/0220179 A1* | 7/2021 | Rebella | A61B 1/227 |

FOREIGN PATENT DOCUMENTS

| | | |
|---|---|---|
| JP | 2004-321478 A | 11/2004 |
| JP | 2005-211231 A | 8/2005 |
| JP | 2006-325690 A | 12/2006 |
| JP | 2012-152246 A | 8/2012 |
| JP | 2016-522717 A | 8/2016 |

* cited by examiner

ENDOSCOPE

CROSS-REFERENCE TO RELATED APPLICATIONS

Priority is claimed from Japanese Patent Application No. 2020-056092, filed on Mar. 26, 2020, the content of which is incorporated herein by reference.

TECHNICAL FIELD

The present invention relates to an endoscope.

BACKGROUND

The following Japanese Unexamined Patent Application, First Publication No. 2002-51968 discloses an ophthalmic electronic endoscope that includes a color index portion for adjusting the white balance of an electronic image of an endoscope inside a protective cap and is capable of adjusting white balance with the protective cap mounted.

However, since the protective cap of the above related art includes the color index portion on a flat surface (bottom surface) having a bottomed tubular shape, there is a case where an inner wall corner portion of the protective cap may be reflected in the angle of view of the endoscope. The corner portion is farther from a central portion of the plane facing the tip of the endoscope that captures a subject image, and the periphery of the corner portion is likely to be dark. As a result, it is difficult to adjust the white balance correctly.

SUMMARY

One or more embodiments of the present invention provide an endoscope capable of correctly adjusting white balance with a protective cap mounted.

An endoscope according to one or more embodiments of the present invention includes an endoscope operation unit; an insertion observation unit that extends forward from the endoscope operation unit; and a detachable protective cap that covers the insertion observation unit. A color index portion for adjusting white balance is provided inside the protective cap at a position facing a tip of the insertion observation unit. The color index portion has a shape including a curved surface in a sectional view in a longitudinal direction of the insertion observation unit.

According to this configuration, since the color index portion inside the protective cap has the shape including the curved surface in the sectional view in the longitudinal direction of the insertion observation unit, the distance from the tip of the insertion observation unit to the color index portion are substantially equal. Therefore, the difference in brightness between a central portion of a flat surface and a peripheral portion thereof becomes smaller than that in a case where the color index portion is the flat surface, and the white balance can be more correctly adjusted.

In the above endoscope, the color index portion may have a hemispherical shape.

In the above endoscope, the color index portion may have a parabolic shape.

In the above endoscope, the color index portion may include a flat surface that faces the tip of the insertion observation unit with a gap in the longitudinal direction, and the curved surface may be provided around the plane.

In the above endoscope, the curved surface may extend from an inside to an outside of an angle of view of the insertion observation unit.

In the above endoscope, the protective cap may be formed of a material for forming the color index portion.

In the above endoscope, an outer surface of the protective cap may be colored black.

According to one or more embodiments of the present invention, it is possible to provide the endoscope capable of correctly adjusting the white balance with the protective cap mounted.

DETAILED DESCRIPTION

Hereinafter, embodiments of the present invention will be described with reference to the drawings. In the following description, an ophthalmic electronic endoscope will be exemplified.

Figure 1:
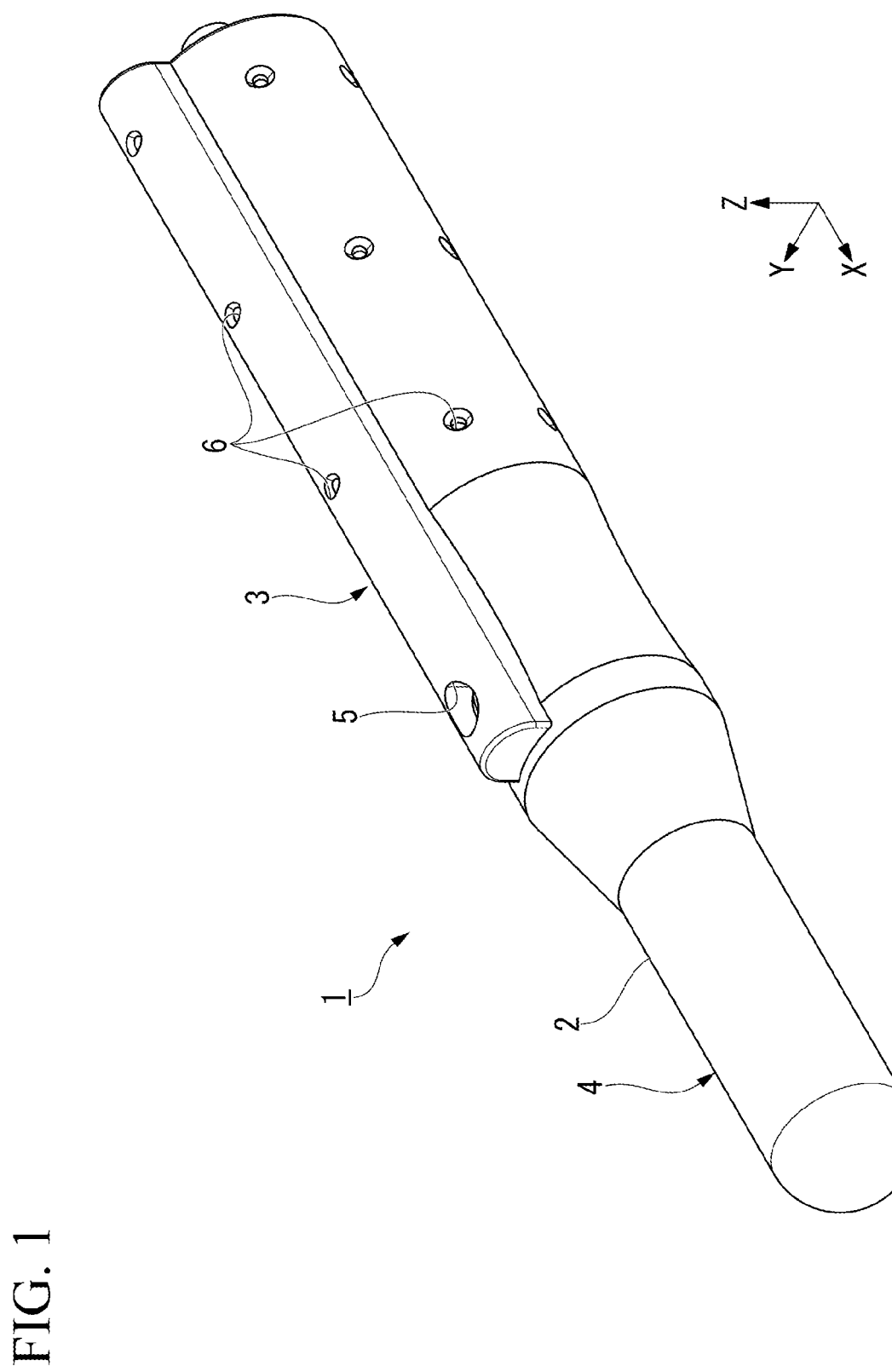
FIG. 1 is a perspective view of an endoscope mounted with a protective cap according to one or more embodiments of the present invention.
Figure 2:
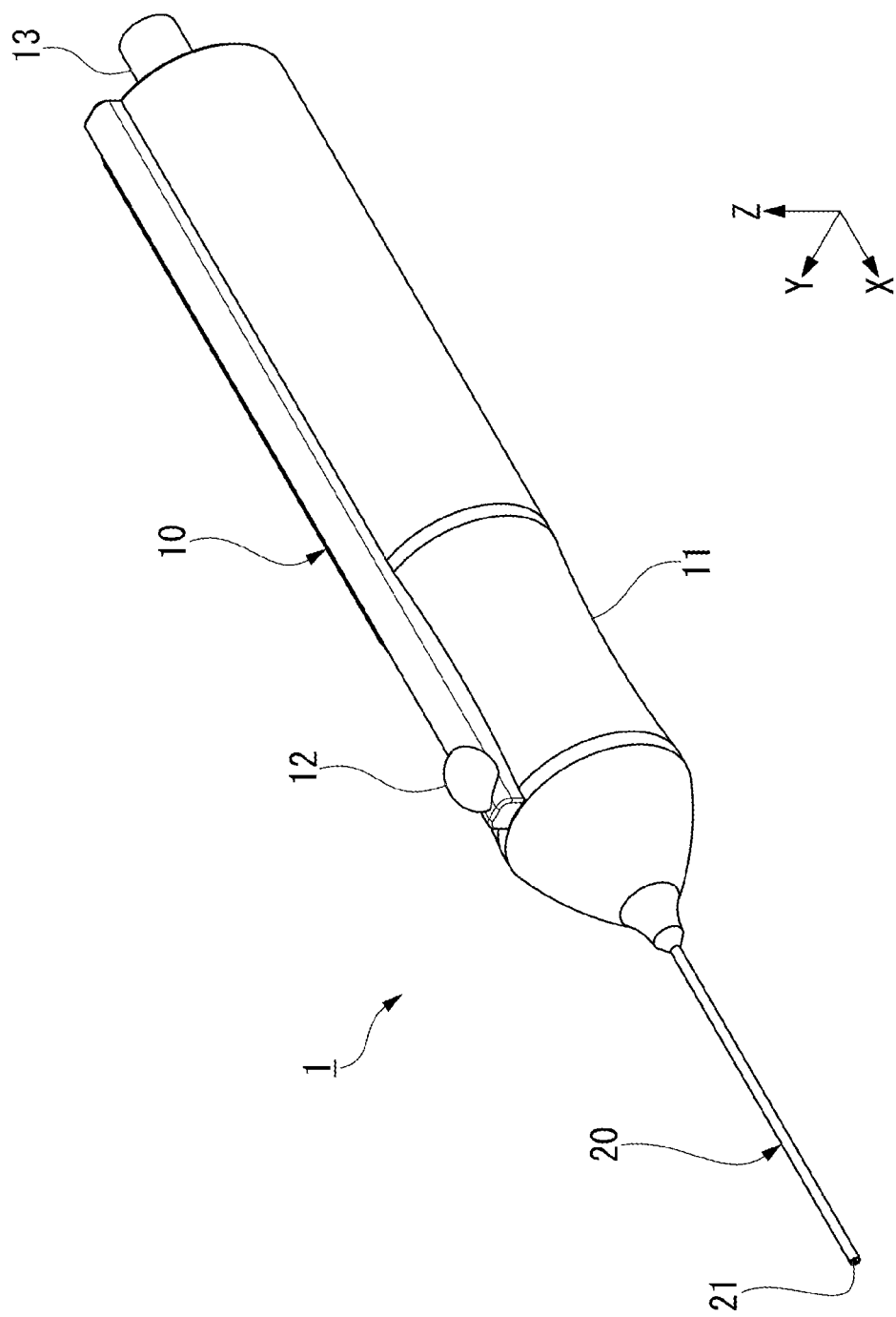
FIG. 2 is a perspective view of the endoscope from which the protective cap according to one or more embodiments of the present invention is removed.
Figure 3:
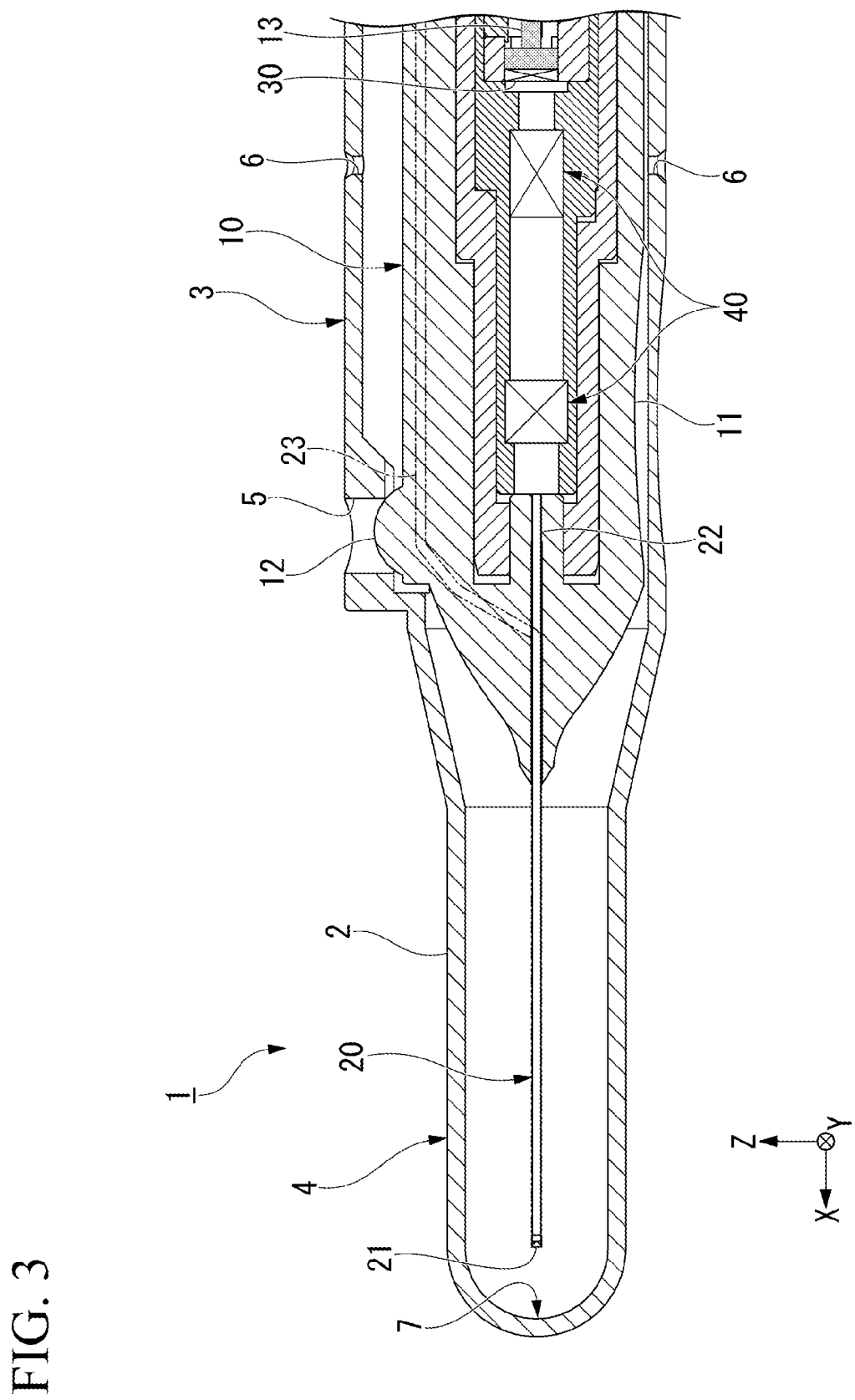
FIG. 3 is a sectional configuration view of the endoscope according to one or more embodiments of the present invention.

FIG. 1 is a perspective view of an endoscope 1 mounted with a protective cap 2 according to one or more embodiments of the present invention. FIG. 2 is a perspective view of the endoscope 1 from which the protective cap 2 according to one or more embodiments of the present invention is removed. FIG. 3 is a sectional configuration view of the endoscope 1 according to one or more embodiments of the present invention.

As shown in these figures, the endoscope 1 includes an endoscope operation unit 10, an insertion observation unit 20 that extends forward from the endoscope operation unit 10, and the protective cap 2 that covers the insertion observation unit 20 and is detachable.

In the following description, the XYZ Cartesian coordinate system may be set, and a positional relationship of respective members may be described with reference to the XYZ Cartesian coordinate system. An X-axis direction is a longitudinal direction in which the insertion observation unit 20 extends, and a Y-axis direction and a Z-axis direction are biaxial orthogonal directions (also referred to as a lateral direction of the insertion observation unit 20) orthogonal to the X-axis direction.

An engagement hole 5 and an engagement protrusion 12 described below are disposed in the Z-axis direction out of the Y-axis direction and the Z-axis direction. Additionally, in the longitudinal direction in which the insertion observation unit 20 extends, the "front" is a tip 21 side (+X side) in the insertion observation unit 20, and the "rear" is a side (−X side, that is, a root side of the insertion observation unit 20) opposite to the tip 21 in the insertion observation unit 20.

As shown in FIGS. 1 and 3, the protective cap 2 includes a mounting portion 3 that is mounted on the endoscope operation unit 10, and a tip accommodation portion 4 that extends forward from the mounting portion 3 and covers the insertion observation unit 20. The mounting portion 3 is formed in a substantially cylindrical shape that surrounds an outer periphery of the endoscope operation unit 10. An engagement hole 5 and a plurality of communication holes 6 are formed on the outer periphery of the mounting portion 3.

As shown in FIG. 1, the engagement hole 5 is formed on a front side of the mounting portion 3. The protective cap 2 is detachably attached, i.e., capable of being attached to the endoscope operation unit 10 and detached from the endoscope operation unit 10. As shown in FIG. 3, the protective cap 2 is mounted on the endoscope operation unit 10 by engaging the engagement protrusion 12 formed on the front side of the endoscope operation unit 10 with the engagement hole 5.

The communication hole 6 is formed behind the engagement hole 5 in the mounting portion 3. In addition, the communication hole 6 may be formed in front of the engagement hole 5 in the mounting portion 3. The communication hole 6 allows sterilization of the endoscope operation unit 10 and the insertion observation unit 20 with the protective cap 2 mounted. That is, a sterilizing gas can flow into the protective cap 2 from the communication hole 6.

As shown in FIG. 3, the tip accommodation portion 4 is formed in a substantially bottomed tubular shape that surrounds the outer periphery and the tip 21 of the insertion observation unit 20 with a gap. A color index portion 7 for adjusting the white balance adjustment of an electronic image (imaging element 30) is provided at a position facing the tip 21 of the insertion observation unit 20 on an inner surface of the tip accommodation portion 4 facing the tip 21 of the insertion observation unit 20 in the longitudinal direction (X-axis direction).

The insertion observation unit 20 is formed in the shape of an elongated needle that extends in the X-axis direction. The tip 21 of the insertion observation unit 20 is provided with an objective lens. The insertion observation unit 20 includes an image fiber 22 (optical fiber) that transmits a subject image acquired through the objective lens to the endoscope operation unit 10, and an illumination fiber 23 (optical fiber) that emits illumination light forward from the tip 21.

The image fiber 22 is disposed inside a hard outer tube (stainless steel pipe or the like) (not shown). The illumination fiber 23 is also disposed inside a hard outer tube, similar to the image fiber 22. The other end of the illumination fiber 23 passes through a subcutaneous portion of an outer surface of the insertion observation unit 20 and is connected to an illumination device (light source) (not shown). In addition, instead of the illumination fiber 23, a small illumination device (LED or the like) may be provided at the tip 21 of the insertion observation unit 20.

As shown in FIG. 2, the endoscope operation unit 10 is formed in a substantially pen shape (also referred to as a substantially columnar shape including a conical portion on a front side) having a holding portion 11 on the front side in the X-axis direction. As shown in FIG. 3, an imaging element 30 such as a CCD or CMOS and a re-imaging optical system 40 for re-imaging the subject image transmitted by the image fiber 22 on the imaging element 30 are provided (disposed) inside the endoscope operation unit 10.

The imaging element 30 converts the re-imaged subject image into electronic image data. As shown in FIG. 2, the electronic image data is transmitted to an image processing device (not shown) via a cable 13 that extends backward from the endoscope operation unit 10. The image processing device displays the electronic image data on a monitor or stores the data in a storage medium.

Figure 4:
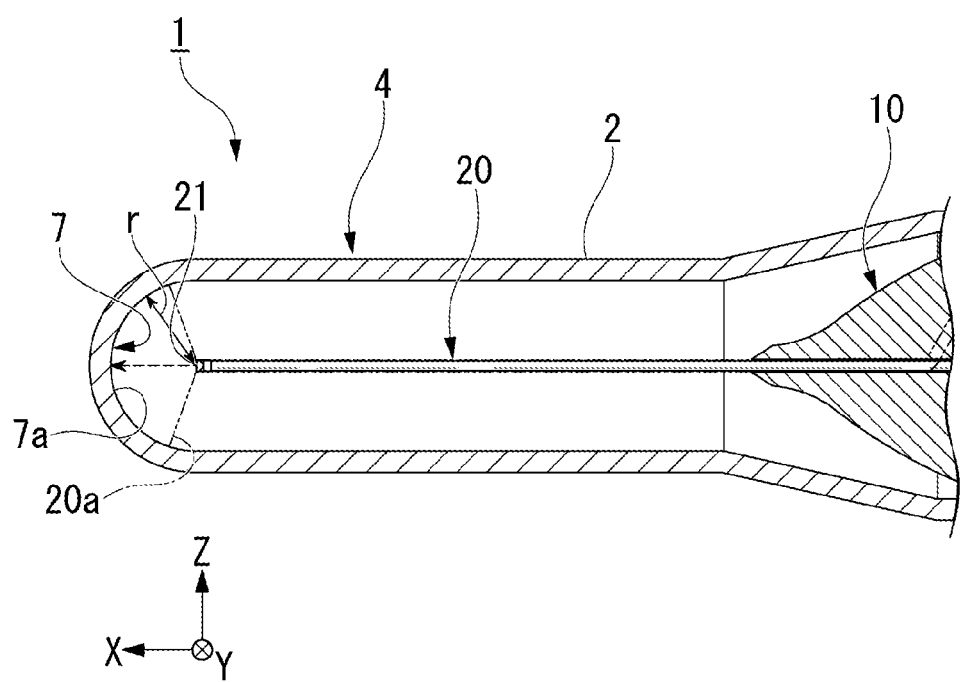
FIG. 4 is a sectional view illustrating the shape of a color index portion according to one or more embodiments of the present invention.

FIG. 4 is a sectional view illustrating the shape of the color index portion 7 according to one or more embodiments of the present invention.

As shown in FIG. 4, the color index portion 7 has a shape including a curved surface 7*a* in a sectional view in the longitudinal direction (X-axis direction) of the insertion observation unit 20. In addition, the "section in the longitudinal direction (X-axis direction) of the insertion observation unit 20" is a section including the X-axis direction, and includes, for example, not only an X-Z plane shown in FIG. 4 but also an X-Y plane.

The color index portion 7 includes the curved surface 7*a* that is convex toward the front of the insertion observation unit 20. The color index portion 7 shown in FIG. 4 has a hemispherical shape having a radius of curvature r centered on the tip 21 of the insertion observation unit 20. The curved surface 7*a* extends from the inside to the outside of the angle of view 20*a* of the insertion observation unit 20 (i.e., the curved surface 7*a* covers at least the angle of view 20*a*). That is, the curved surface 7*a* is formed from the inside to the outside (rear) of the observation region that can be acquired from the tip 21 of the insertion observation unit 20 via the objective lens.

The protective cap 2 according to one or more embodiments is formed of a material that forms the color index portion 7. For example, the protective cap 2 is molded of a resin material containing a reference color coloring material for adjusting the white balance of the insertion observation unit 20. That is, the entire inner surface of the protective cap 2 including the curved surface 7*a* is formed with the reference color for adjusting the white balance of the insertion observation unit 20. In this case, the color index portion 7 refers to a range reflected in an angle of view 20*a* of the insertion observation unit 20 in a state where the protective cap 2 is not removed.

In addition, the color index portion 7 may be molded of a separate member from the protective cap 2 and mounted on a bottomed portion of the protective cap 2. Additionally, the color index portion 7 may be formed on the bottomed portion of the protective cap 2 by painting.

According to the endoscope 1 having the above configuration, the color index portion 7 inside the protective cap 2 has a shape including the curved surface 7*a* in a sectional view in the longitudinal direction of the insertion observation unit 20, so that the distance from the tip 21 of the insertion observation unit 20 to the color index portion 7 is equal or substantially equal. Accordingly, the difference in brightness between a central portion of a flat surface and a peripheral portion thereof becomes smaller than that in a case where the color index portion 7 is the flat surface, and the white balance can be more correctly adjusted.

In this way, according to the above-described one or more embodiments, the endoscope 1 capable of correctly adjusting the white balance with the protective cap 2 mounted can be provided by including the endoscope operation unit 10, the insertion observation unit 20 that extends forward from the endoscope operation unit 10, and the detachable protective cap 2 that covers the insertion observation unit 20 and by adopting a configuration in which the color index portion 7 for adjusting the white balance is provided inside the protective cap 2 at the position facing the tip 21 of the insertion observation unit 20 and the color index portion 7 has a shape including the curved surface 7a in the sectional view in the longitudinal direction (X-axis direction) of the insertion observation unit 20. Additionally, the protective cap 2 has a plurality of the communication holes 6, and the endoscope operation unit 10 and the insertion observation unit 20 can be sterilized with the protective cap 2 mounted.

Additionally, in one or more embodiments, the color index portion 7 has a hemispherical shape. According to this configuration, since the distance from the tip 21 of the insertion observation unit 20 to the color index portion 7 is equal, the difference in brightness between the central portion of the color index portion 7 facing the tip 21 of the insertion observation unit 20 and the peripheral portion thereof is almost eliminated, and the white balance can be more correctly adjusted.

Additionally, in one or more embodiments, the curved surface 7a of the color index portion 7 extends from the inside to the outside of the angle of view 20a of the insertion observation unit 20. According to this configuration, since an inner wall corner portion of the protective cap 2 is not reflected in the angle of view 20a of the insertion observation unit 20, shadows are less likely to be formed in the angle of view 20a, and the white balance can be more correctly adjusted.

Additionally, in one or more embodiments, the protective cap 2 is formed of a material for forming the color index portion 7. According to this configuration, since the inner surface of the protective cap 2 serves as the color index portion 7, the color index portion 7 having a shape including the curved surface 7a in the sectional view in the longitudinal direction (X-axis direction) of the insertion observation unit 20 can be accurately formed as compared to the case where the color index portion 7 is formed by the separate member or formed by the painting.

Additionally, in one or more embodiments, the configurations as shown in FIGS. 5 to 8 may be adopted. In addition, in the following description, the same or equivalent components as those in one or more of the above-described embodiments are designated by the same reference signs, and the description thereof will be simplified or omitted.

Figure 5:
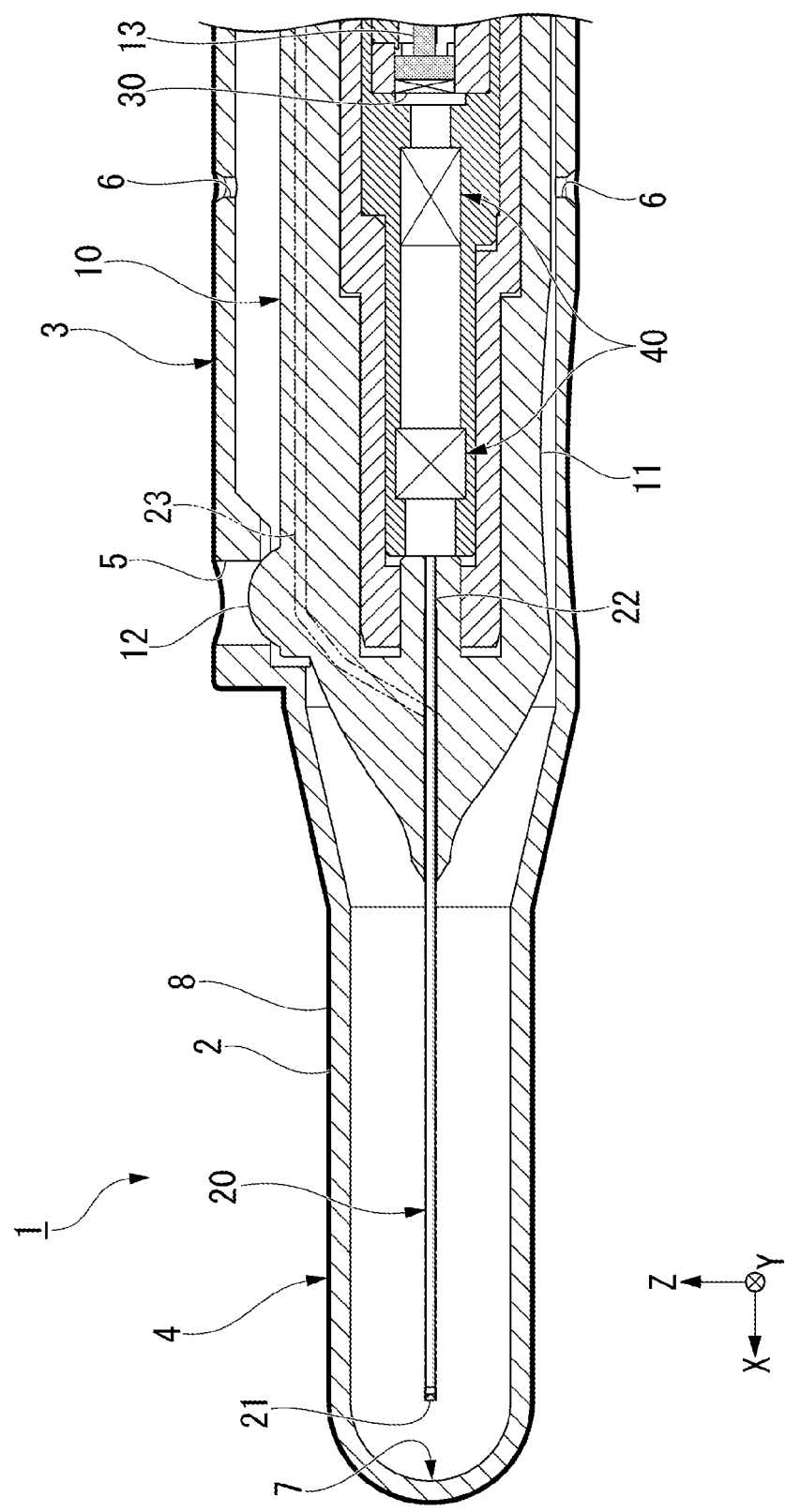
FIG. 5 is a sectional configuration view of an endoscope according to a modification example of one or more embodiments of the present inventions.

FIG. 5 is a sectional configuration view of the endoscope 1 according to a modification example of one or more embodiments.

The protective cap 2 shown in FIG. 5 has a black coating 8 applied to the entire outer surface thereof. That is, the outer surface of the protective cap 2 is colored black. According to this configuration, it is possible to suppress indoor light (outside light) outside the protective cap 2 from being transmitted through the protective cap 2 and entering the inside thereof. For this reason, the white balance can be more correctly adjusted with the protective cap 2 mounted.

Figure 6:
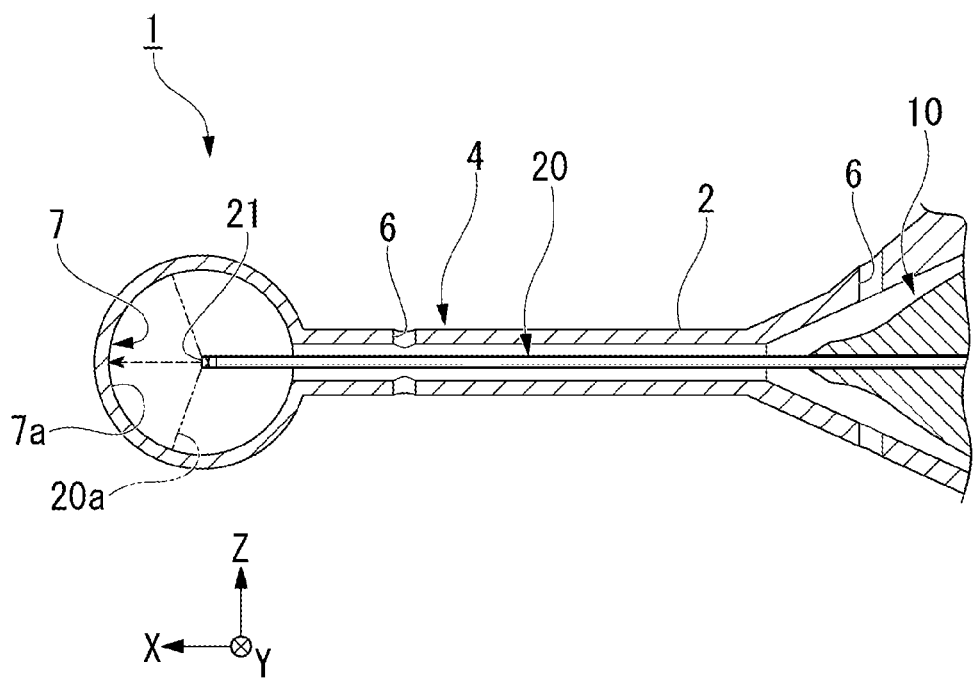
FIG. 6 is a sectional view illustrating the shape of the color index portion according to a modification example of one or more embodiments of the present invention.

FIG. 6 is a sectional view illustrating the shape of the color index portion 7 according to a modification example of one or more embodiments.

The color index portion 7 shown in FIG. 6 has a spherical shape centered on the tip 21 of the insertion observation unit 20. The curved surface 7a of the color index portion 7 extends to the rear of the tip 21 of the insertion observation unit 20. According to this configuration, the white balance can be correctly adjusted even in a case where the angle of view 20a of the insertion observation unit 20 is wide. In addition, in this case, a communication hole 6 for steriliza- tion may be formed at the position of the color index portion 7 (sphere) where outside light also does not enter in the tip accommodation portion 4 of the protective cap 2.

Figure 7:
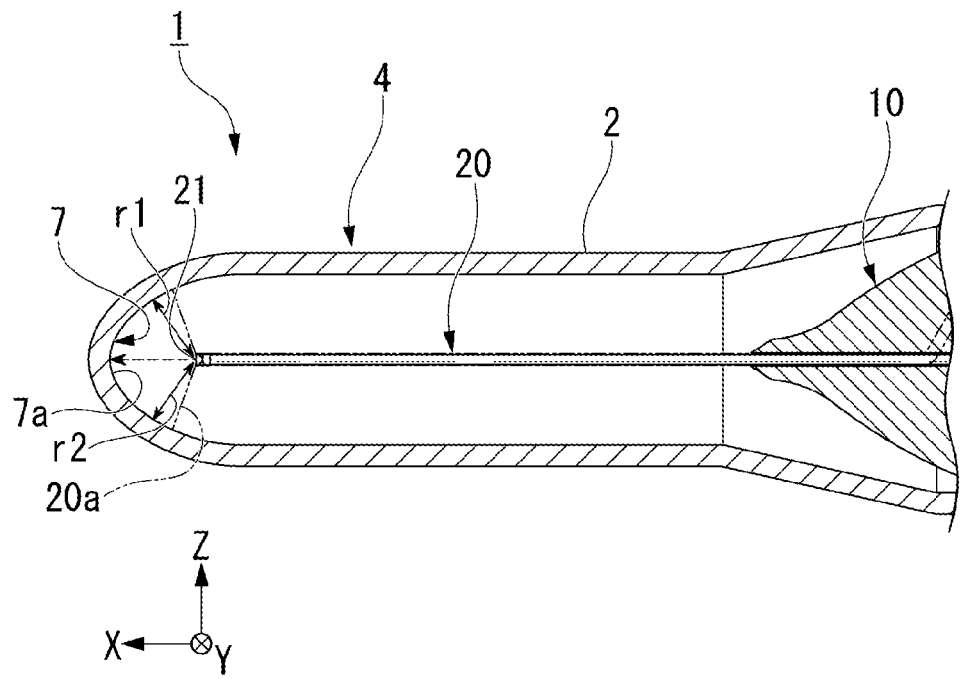
FIG. 7 is a sectional view illustrating the shape of the color index portion according to a modification example of one or more embodiments of the present invention.

FIG. 7 is a sectional view illustrating the shape of the color index portion 7 according to a modification example of one or more embodiments.

The color index portion 7 shown in FIG. 7 has a parabolic shape having the tip 21 of the insertion observation unit 20 as a focal point. According to this configuration, the distance from the tip 21 of the insertion observation unit 20 to the color index portion 7 becomes substantially equal, and the inner wall corner portion of the protective cap 2 is not reflected in the angle of view 20a of the insertion observation unit 20. Therefore, the white balance can be more correctly adjusted. In addition, for example, the radii of curvature r1 and r2 on an upper side and a lower side of the curved surface 7a may be changed with a center line passing through the tip 21 of the insertion observation unit 20 as a boundary.

Figure 8:
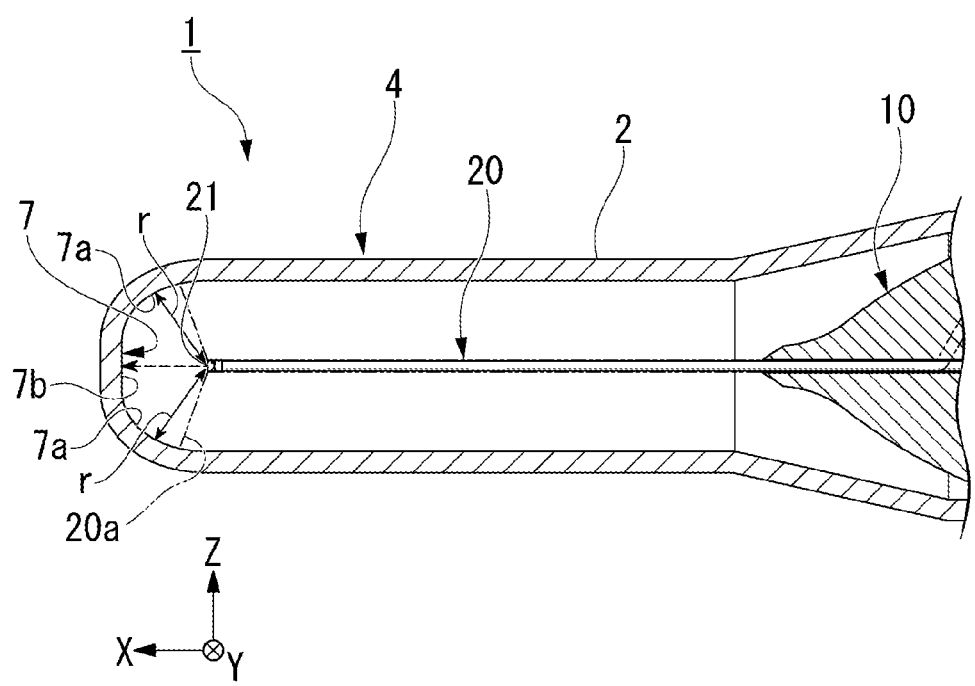
FIG. 8 is a sectional view illustrating the shape of the color index portion according to a modification example of one or more embodiments of the present invention.

FIG. 8 is a sectional view illustrating the shape of the color index portion 7 according to a modification example of one or more embodiments.

The color index portion 7 shown in FIG. 8 includes a flat surface 7b facing the tip 21 of the insertion observation unit 20 with a gap in the longitudinal direction, and the curved surface 7a is provided at both ends of the flat surface 7b (i.e., the flat surface 7b extends from the curved surface 7a). According to this configuration, the flat surface 7b of the central portion of the color index portion 7 and the curved surface 7a at the peripheral portion thereof are not equal or substantially equal with respect to the tip 21 of the insertion observation unit 20. However, since the inner wall corner portion of the protective cap 2 is not reflected in the angle of view 20a (the right angle in the related art disappears and the curved surface 7a is obtained) of the insertion observation unit 20, the white balance can be more correctly adjusted.

While embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope comprising:
    an endoscope operation unit;
    an insertion observation unit that extends forward from the endoscope operation unit in a longitudinal direction; and
    a protective cap that covers the insertion observation unit and is detachably attached to the endoscope operation unit, wherein
    the protective cap comprises a color index portion for adjusting white balance,
    the color index portion is disposed inside the protective cap at a position facing a tip of the insertion observation unit,
    the color index portion comprises a curved surface in a sectional view in the longitudinal direction of the insertion observation unit,
    the protective cap is engaged with the endoscope operation unit,
    the protective cap is made of a same material as the color index portion, the protective cap and the color index portion are integrally formed, the curved surface has a radius of curvature centered at the tip of the insertion observation unit, a distance between the curved surface and the tip of the insertion observation unit is constant throughout an entire length of the curved surface, and the curved surface has a hemispherical shape that is convex away from the insertion observation unit.

2. The endoscope according to claim 1, wherein the color index portion further comprises a flat surface that extends from the curved surface and faces the tip of the insertion observation unit with a gap in the longitudinal direction.

3. The endoscope according to claim 1, wherein the curved surface covers at least an angle of view of the insertion observation unit.

4. The endoscope according to claim 1, wherein a color of an outer surface of the protective cap is black.

5. The endoscope according to claim 1, wherein the protective cap:

has an engagement part that engages with the endoscope operation unit, and covers an outer periphery of the endoscope operation unit.

6. An endoscope comprising:

an endoscope operation unit;

an insertion observation unit that extends forward from the endoscope operation unit in a longitudinal direction; and a protective cap that covers the insertion observation unit and is detachably attached to the endoscope operation unit, wherein the protective cap comprises a color index portion for adjusting white balance, the color index portion is disposed inside the protective cap at a position facing a tip of the insertion observation unit, the color index portion comprises a curved surface in a sectional view in the longitudinal direction of the insertion observation unit, the protective cap is engaged with the endoscope operation unit, the protective cap is made of a same material as the color index portion, the protective cap and the color index portion are integrally formed, the curved surface has a radius of curvature centered at the tip of the insertion observation unit, the curved surface is a parabolic surface having a focal point of the parabolic surface at the tip of the insertion observation unit, and the curved surface is convex away from the insertion observation unit.

7. The endoscope according to claim 6, wherein the protective cap:

has an engagement part that engages with the endoscope operation unit, and covers an outer periphery of the endoscope operation unit.

\* \* \* \* \*